United States Patent
Conroy

(10) Patent No.: US 8,837,683 B2
(45) Date of Patent: Sep. 16, 2014

(54) CRITICAL HEALTH INFORMATION PROFILE AND EMERGENCY COMMUNICATION SYSTEM

(75) Inventor: Thomas M. Conroy, Redondo Beach, CA (US)

(73) Assignee: Medsign International Corporation, West Palm Beach, FL (US)

( * ) Notice: Subject to any disclaimer, the term of this patent is extended or adjusted under 35 U.S.C. 154(b) by 437 days.

(21) Appl. No.: 13/006,139

(22) Filed: Jan. 13, 2011

(65) Prior Publication Data
US 2012/0088466 A1    Apr. 12, 2012

Related U.S. Application Data

(60) Provisional application No. 61/391,653, filed on Oct. 10, 2010.

(51) Int. Cl.
*H04M 11/04* (2006.01)
*G06F 19/00* (2011.01)

(52) U.S. Cl.
CPC .......... *G06F 19/322* (2013.01); *G06F 19/3418* (2013.01); *G06F 19/323* (2013.01)
USPC .................. 379/38; 379/40; 379/41; 379/42; 379/45; 379/52

(58) Field of Classification Search
USPC .................................... 379/38–49; 455/404.1
See application file for complete search history.

(56) References Cited

U.S. PATENT DOCUMENTS

| | | |
|---|---|---|
| 3,989,900 A | 11/1976 | Dibner |
| 4,064,368 A | 12/1977 | Dibner |
| 4,068,097 A | 1/1978 | Verriest |
| 4,371,751 A | 2/1983 | Hilligoss, Jr. et al. |
| 4,467,142 A | 8/1984 | Rupp et al. |
| 4,510,350 A | 4/1985 | Wagner et al. |
| 4,523,307 A | 6/1985 | Brown et al. |
| 4,524,243 A | 6/1985 | Shapiro |

(Continued)

FOREIGN PATENT DOCUMENTS

| | | |
|---|---|---|
| WO | WO2007125322 | 11/2007 |
| WO | WO2009032134 | 3/2009 |
| WO | WO2010038156 | 4/2010 |

*Primary Examiner* — Joseph J Nguyen

(57) ABSTRACT

A microprocessor-based emergency response communication system used to call and communicate with the 9-1-1 operator and also allows emergency responder's immediate access to a user's Critical Health Information Profile stored in the device at the point and location of crisis. The device is used to create individual Critical Health Information Profiles which is Health Level-7 compliant enabling it to seamlessly communicate with major hospital networks worldwide. This functional capability provides a system that can retrieve and transmit user-stored personal and health information by emergency responders at the point of care. The emergency responder can access the customer's Critical Health Information Profile database, review the data for pertinent information and then transmit that data to a designated receiving hospital or medical center. The device provides an electronic means of dialing and communicating directly with the 9-1-1 operator. A wireless remote transmitter unit can be activated from the wireless transmitter or the base unit to dial and connect with the 9-1-1 operator, broadcast a canned message with or without a personal-recorded message, and personally communicate with the 9-1-1 operator through a two-way speakerphone system. The device contains software enabling the user and medical personnel the ability to input, store, retrieve and analyze the user's vital sign data and other pertinent health information.

27 Claims, 14 Drawing Sheets

(56) References Cited

U.S. PATENT DOCUMENTS

| | | |
|---|---|---|
| 4,571,455 A | 2/1986 | Labock et al. |
| 4,577,182 A | 3/1986 | Millsap et al. |
| 4,724,538 A | 2/1988 | Farrell |
| 4,760,593 A | 7/1988 | Shapiro et al. |
| 4,764,757 A | 8/1988 | DeMarco et al. |
| 4,799,156 A | 1/1989 | Shavit et al. |
| 4,866,764 A | 9/1989 | Barker |
| 4,884,059 A | 11/1989 | Shapiro |
| 4,884,060 A | 11/1989 | Shapiro |
| 4,887,291 A | 12/1989 | Stillwell |
| 4,908,602 A | 3/1990 | Reich et al. |
| 4,918,717 A | 4/1990 | Bissonnette et al. |
| 4,951,196 A | 8/1990 | Jackson |
| 4,993,058 A | 2/1991 | McMinn et al. |
| 5,305,370 A | 4/1994 | Kearns et al. |
| 5,664,109 A | 9/1997 | Johnson et al. |
| 5,710,551 A | 1/1998 | Ridgeway |
| 5,758,126 A | 5/1998 | Daniels et al. |
| 5,829,001 A | 10/1998 | Li et al. |
| 5,995,939 A | 11/1999 | Berman et al. |
| 2004/0172290 A1* | 9/2004 | Leven ............... 705/2 |
| 2006/0205416 A1* | 9/2006 | Kayzar et al. ............ 455/456.1 |
| 2007/0035403 A1* | 2/2007 | Krishna et al. ............ 340/573.1 |
| 2007/0242424 A1* | 10/2007 | Lieu et al. ............ 361/686 |
| 2008/0212746 A1* | 9/2008 | Gupta et al. ............ 379/38 |
| 2008/0220814 A1* | 9/2008 | Hedtke et al. ............ 455/556.1 |
| 2009/0097474 A1* | 4/2009 | Ray et al. ............ 370/352 |
| 2009/0177495 A1* | 7/2009 | Abousy et al. ............ 705/3 |
| 2011/0059719 A1* | 3/2011 | Spielvogel et al. ............ 455/404.1 |
| 2011/0161172 A1* | 6/2011 | Lee ............ 705/14.55 |
| 2011/0260873 A1* | 10/2011 | Ouchi ............ 340/573.3 |
| 2012/0179856 A1* | 7/2012 | Smith, Jr. ............ 711/103 |
| 2012/0282884 A1* | 11/2012 | Sun ............ 455/404.2 |

\* cited by examiner

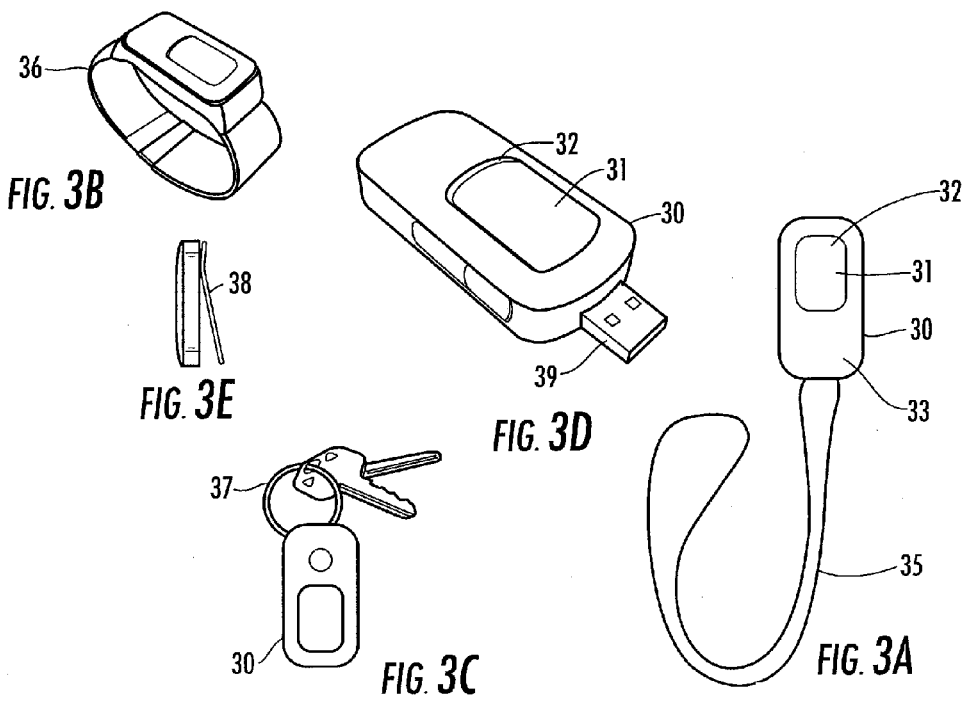
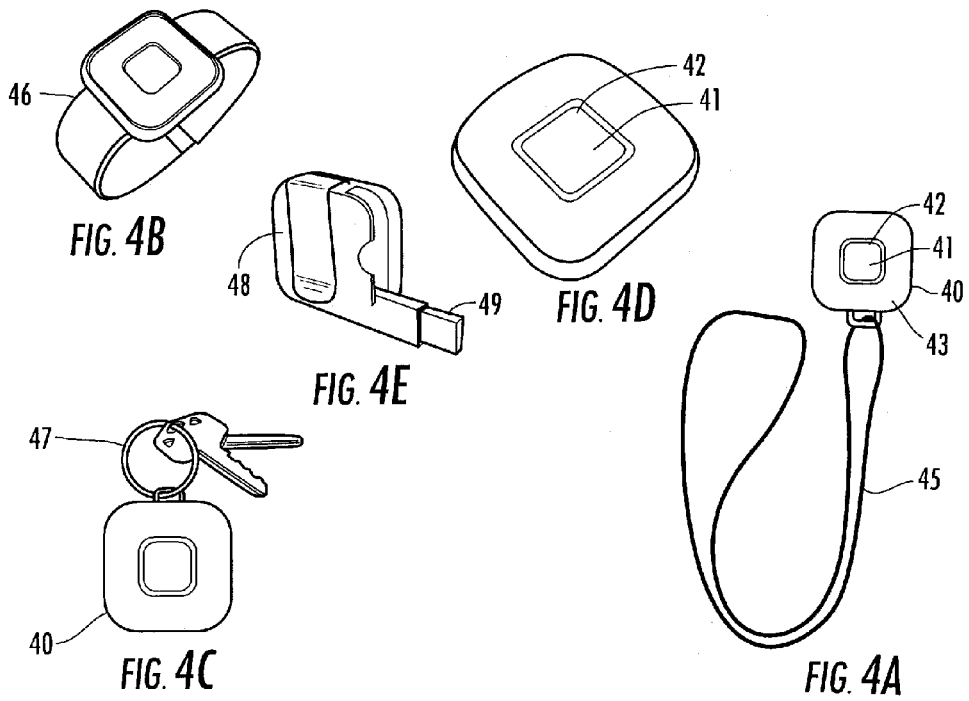

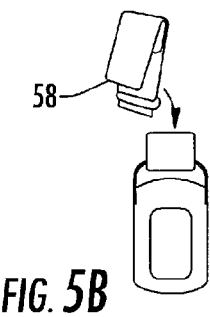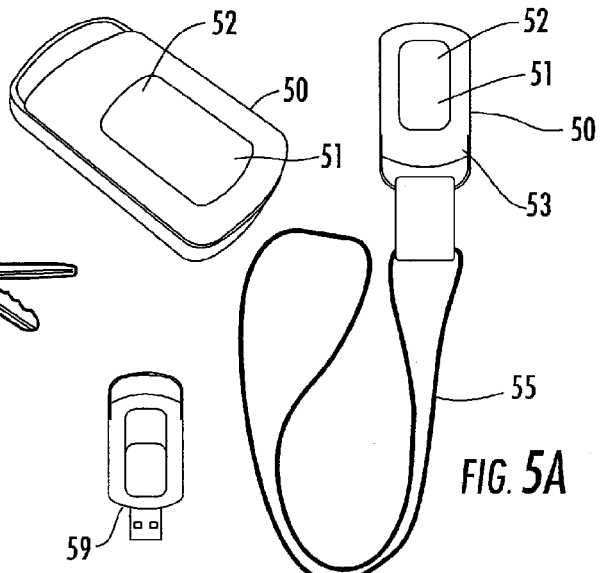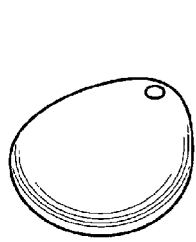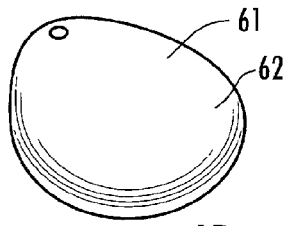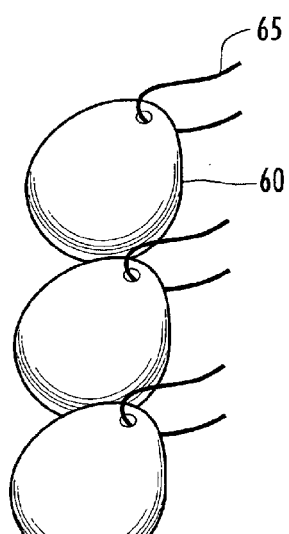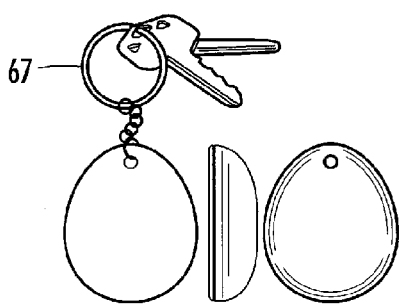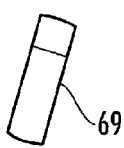

EXAMPLE OF A CRITICAL HEALTH INFORMATION PROFILE
AS SEEN ON THE LCD TOUCH SCREEN, DESKTOP, LAPTOP OR
OTHER PERSONAL DEVICES WITH AN LCD SCREEN.

CRITICAL HEALTH INFORMATION PROFILE AND EMERGENCY COMMUNICATION SYSTEM

CROSS REFERENCE TO RELATED APPLICATIONS

This application claims benefit of the filing date of U.S. Provisional Patent Application No. 61/391,653, filed on Oct. 10, 2010, the contents of which are herein incorporated by reference.

FIELD OF THE INVENTION

The invention is directed to the field of emergency communications and, in particular, to a communication system that facilitates an emergency response and provide the health information profile of a patient to a first responder.

BACKGROUND OF INVENTION

Accidents happen often and without warning, and when they do the speed of response and access of critical user information determines their survivability. The sooner that a first responder can treat an emergency situation, and the more information the first responder has access to regarding the person who is in a crisis situation, the better the chance of minimizing the risk of permanent damage, disability or even death.

Each year, about 1.1 million Americans suffer a heart attack. About 460,000 of those attacks are fatal. About half of those deaths occur within 1-2 hours of the start of the symptoms and before the person reaches the hospital. The sooner a patient receives medical attention, and the more personal health information known about the patient, the higher probability of surviving and preventing the permanent damage. The Journal of the American Heart Association revealed that those who received lifesaving, clot-busting therapy within the first hour of a heart attack can almost triple their chance of survival. While heart attacks are at the top of the list, strokes, seizures and personal injuries resulting from accidents are also leading causes for loss of life.

While numerous companies have marketed fee-based patient monitoring systems, there are no known systems that can access the 9-1-1 emergency system directly and provide timely critical health information to the first responder without going through a middle-man for patient information. A review of more than 30 emergency responders demonstrate that not one of them calls the third party vendors for patient information. There are several reasons, but the first is that time is of the essence, and if the information is not in front of them it is considered useless. The second most important reason is because 'a third party' is involved and the information could be inaccurate which could create a liability on the responder's part. Therefore, unless the information is reliable and readily accessible to the first responder, or in the possession of the patient, the first responder will not use the information.

There are companies that have marketed an emergency response system that will dial 9-1-1. Advance versions may even provide two-way speakerphone communication. However, no known companies have produced an emergency communication system with a digital personal health information subsystem incorporated into it's device that can be accessed by emergency responders at the time of crisis.

Current medical record systems are oriented toward a centralized process of storing and retrieving a User's electronic medical record system. Numerous products exist that are based upon complex and complicated systems that require the information to be located on a centralized server which is accessed through the Internet. In order to retrieve electronic medical records of a particular individual, the User, or those approved by the user (such as emergency responders or paramedics), must provide the proper user name and password of the person in the crisis to get to this information in a time of crisis. If the User is incapacitated and is unable to provide a user name or password, the emergency responder would not receive the critical medical information. If the User is located in an area where the emergency responders are unable to access the Internet, the emergency responder will not receive the critical medical information that could mean the difference between life and death of the User.

In addition, it is well recognized that the public's lack of confidence in the Internet and its ability to prevent hackers from accessing their personal and medical information inhibits most all attempts at placing ones medical history in an area accessible to first responders. Studies have shown, and common sense states, that the public does not want their personal information accessible by unapproved persons; and as a result, there has been a lack of business growth in systems that provide such a service that is located on the Internet. While a de-centralized system provides an alternative, to date there has been a lack of attention paid to develop a process by which the information is distributed and in the hands of its Users rather than centralized on a server on the Internet.

Thus, what is needed in the industry is an emergency communication system with a digital personal health information subsystem incorporated into a device that can be accessed by emergency responders at the time of crisis, the device providing direct connection with a 9-1-1 operator and allowing hands free communication.

SUMMARY OF THE INVENTION

Disclosed is a personal emergency response device using uniquely designed hardware and software driven processes to provide a dynamic methodology for contacting and communicating with 9-1-1 Operators, providing emergency responders with immediate access to a User's personal Critical Health Information Profile at the point and location of crisis, and providing interactive applications developed toward providing remote medical and prescriptive services.

The instant invention allows the User to have complete control of their personal and health information, and this includes the information available for use and the location of where this information is placed, stored, and accessed. With the User having access to emergency communication systems and their own health record at the location of crisis in one computer-based device, the device presents an opportunity to provide additional services to the User that do not exist today in a single functional system.

The device incorporates a microprocessor-based emergency response communication system and software technologies that are used to call and communicate with a 9-1-1 operator. Emergency responders have immediate access to a User's Critical Health Information Profile stored in the device at the location of a crisis. The device provides two major functional capabilities in one unit. First, the device has a base unit that incorporates a microprocessor and memory system that uses software to create individual Critical Health Information Profiles. This software is Health Level-7 compliant, enabling seamless communication with major hospital networks worldwide. This functional capability provides a method and system that can retrieve and transmit User-stored personal and health information by emergency responders at the point of care. Using the base unit's LCD touch screen, the emergency responder can access the customer's Critical Health Information Profile database, review the data for pertinent information and then transmit that data to a designated receiving hospital or medical center. A user can securely access, create, edit, delete, store, upload, download and remotely retrieve their Critical Health Information Profile at any time of the day and transmit it to a receiving hospital or medical center either by themselves or a designated person, such as an emergency responder. Second, the device provides an electronic means of dialing and communicating directly with the 9-1-1 operator. This portion of the device is composed of the base unit with specifically design hardwired keys, and a wireless remote transmitter unit that, when set up in the home, office, hotel, yacht or in any location with a telephone network system, can be activated from the wireless transmitter or the base unit to dial and connect with the 9-1-1 operator, broadcast a canned message with or without a personal-recorded message, and personally communicate with the 9-1-1 operator through a two-way speakerphone system. Third, the device contains software enabling the user and medical personnel the ability to input, store, retrieve and analyze the user's vital sign data and other pertinent health information.

An advantage of the instant invention is that it provides three major functional capabilities in one device. The device has a base unit that incorporates specific hardware with hardwired button functions and a microprocessor and memory-based system that is able to call and communicate with the 9-1-1 system.

Another advantage of the instant invention is that when the transmitter is activated, it communicates with the base unit and calls the 9-1-1 system.

Yet another advantage of the instant invention is that the device employs User friendly software to create individual Critical Health Information Profiles and communicates that information through the base unit's LCD touch screen so that emergency responders can access, review, and transmit it effectively and efficiently to a forwarding hospital or medical center in a time of personal crisis.

Still another advantage of the instant invention is to provide a device that contains software enabling the user and medical personnel the ability to input, store, retrieve and analyze the user's vital sign data and other pertinent health information.

An objective of the instant invention is to provide a better system, methodology and process to help those persons who need critical emergency services by providing a device that provides a more efficient and effective means to store and access a User's personal health information, which can be retrieved and used by emergency responders at the point and time of crisis.

Still another objective of the invention is to provide an emergency response device that provides a faster, more effective means of notifying a 9-1-1 operator and providing them with vital information that emergency assistance is required and needed immediately.

Another objective of the instant invention is to provide a method in which the information stored is Health Level-7 software compliant. HL-7 is an internationally based standard for electronic interchange of clinical, financial, and administrative information among health care oriented computer systems.

Still another objective of the instant invention is to provide a system that incorporates HL-7 standards to enables the User's information to be exchanged, integrated, shared, retrieved, delivered and evaluated by HL-7 compliant health services around the world.

Yet another objective of the instant invention is to provide a system that allows emergency responders the ability to forward the user's critical information profile to the receiving medical center in a seamless fashion, thus creating effectiveness and efficiencies not yet seen to date.

Still another objective of the instant invention is to provide a system that allows the administration, financial, and medical services to have instant information of the incoming patient thereby preparing them before the patient's arrival.

Still another objective of the instant invention is to provide a streamline method and process of performing personal emergency response services.

Yet still another objective of the instant invention is to provide a personal emergency response system having a microprocessor and memory system, an LCD touch screen, a power supply, an antenna system for communicating with the system's wireless transmitters, connection ports to access external communication networks, a DC backup power supply, an integrated test system and LED indicator lights to ensure a safe and reliable system, a camera and speakerphone system that permits visual and audio telecommunication, and hardwired hotkey buttons that when activated, perform specific emergency services.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE DRAWINGS

FIG. 3A-3E illustrates a transmitter of a first embodiment;

FIG. 4A-4E illustrates a transmitter of a second embodiment;

FIG. 5A-5E illustrates a transmitter of a third embodiment;

FIG. 6A-6E illustrates a transmitter of a fourth embodiment;

DETAILED DESCRIPTION OF THE PREFERRED EMBODIMENT

The present invention will be described as it applies to its preferred embodiment. It is not intended that the present invention be limited to the described embodiment. It is intended that the invention cover all modifications and alternatives, which may be included within the spirit and scope of the invention. The system is composed of a base unit and wireless transmitters.

Figure 1:
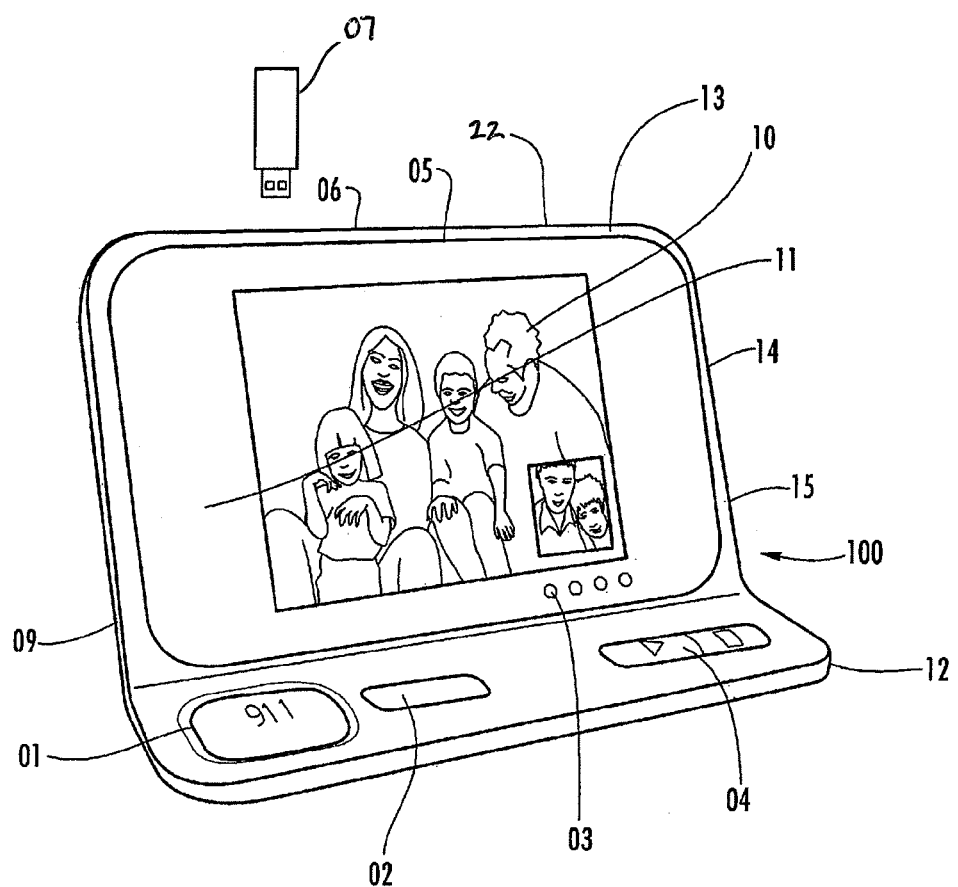
FIG. 1 is a pictorial view of the base unit of the instant invention.
Figure 2:
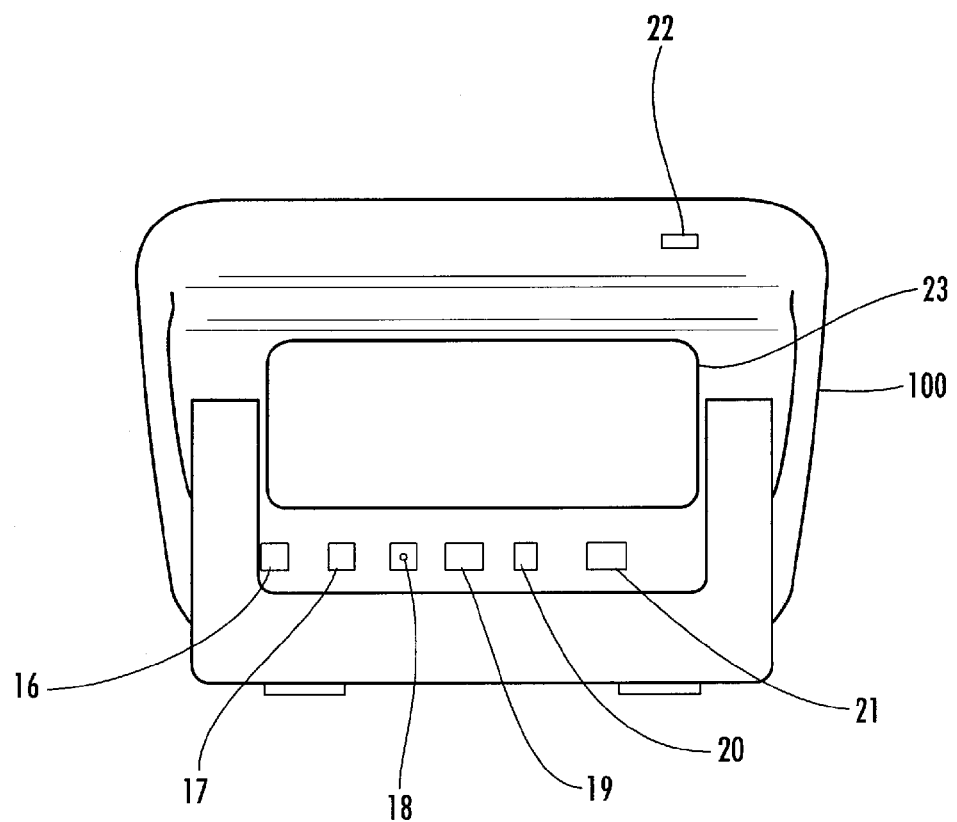
FIG. 2 is a rear view of the base unit.

Now referring to FIGS. 1-2, the Critical Health Information Profile and Emergency Communication System provides an electronic means of dialing and communicating directly with the 9-1-1 operator. A base unit 100 would normally be placed on a desk or table near the telephone wall plate that connects to a telephone or broadband network. In appearance, the base unit device has been designed for use by senior citizens and the medically challenged. It has the following, but is not limited to the following characteristics:

CALL 9-1-1 button (01) is a large, LED lit concave button that when pressed, activates a sequence of events that (i) starts a 5 to 60 second countdown with alarms and flashing lights on the base unit to warn those within range that the 9-1-1 sequence has been activated, (ii) at the completion of the countdown calls 9-1-1 through either a Plain Old Telephone System (POTS), cable network or broadband system, (iii) upon connection with the 9-1-1 operator, the base unit starts and plays the Emergency Message, a combination of a pre-recorded Critical Health Information Profile and Emergency Communication System and User personal message, to the operator, and (iv) continues communication with the 9-1-1 Operator until either the Operator hangs up or the User hangs up the system.

STOP button (02) is a uniquely-designed button which allows the user to distinguish it from the 9-1-1 Call button when pressed, and disengages the User from the 9-1-1 call or other calls that may be in process. The STOP key also performs the transmitter 'PAIRING' function that, when pressed and held for five seconds along with holding the transmitter 'STOP' button for five seconds, sends the system into a sequence that processes the transmitter data along with the base unit data to create a permanent transmission link between the two devices.

Four LED lights (03) are used to indicate status of AC power, internal DC power, telephone line connectivity, and internal system check. A speakerphone system allows the operator to communicate with the user. This occurs once the operator activates the system by pressing "0" on their telephone.

Record/Play Button (04) when pressed and held allows the User to record their personal message that is to be played back to the operator during the Emergency Message sequence. This information is stored in the base unit's memory system. When released, the recently recorded message is played back to the User. If the User desired to re-record the message, they would only have to press and hold the Record button which records the new message over the old message. No other functions are required if the User desires to keep the present message. When the Record/Play Button (04) is pressed, it replays the latest personal Emergency Message recorded by the User. An LED light near the Record button indicates that the user is recording their message.

A video camera (05) enables two-way visual communication. A microphone (06) allows communication between the base unit and the telephone line or broadband system.

A portable, USB-enabled memory stick (07) embedded at the top of the base unit to provide a secondary storage of an exact duplicate of the User's Critical Health Information Profile information. This memory stick can be extracted, transported and accessed by emergency responders as required.

A conventional USB connector port (09) is positioned along the left side of the case. Along the right side of the case is located a screen brightness control (14) and a volume control (15).

The base unit display is preferably an LCD touch screen (10) which allows the User or emergency responder to access the Critical Health Information Profile stored inside the device. Using the graphic interface icons, the emergency responder can dial and connect to a hospital or medical center's HL-7 compliant computer-based network and upload the customer's Critical Health Information Profile right into its system. Because the Critical Health Information Profile system's software is compliant with most hospital's, it will integrate seamlessly with the receiving medical center allowing them to seamlessly create and fill in records for the incoming patient. This can be accomplished either through the POTS or internet interfaces.

A Speaker System (11) allows for receipt of communications through the Critical Health Information Profile and Emergency Communication System's software system.

The shape of the case (12), having an angular positioned screen is designed to permit ease of visualization and access to the 9-1-1 button should a user be wheelchair bound or crawling to the device.

An antenna system (13), while not visible to the user, is directly connected to the face plate of the device to enhance communication connections with the wireless transmitters.

System Operational Characteristics:

LED Indicators. There are four indicator lights on the base unit's front plate. They perform the following functions:
  (1) Low Battery Situation: If the 9V Alkaline battery goes below operating voltage, the system will light up the LOW BATTERY LED on the unit and continue to emit a distinctive "CHIRPING" BEEP every 15 seconds. Replacing the 9V battery will discontinue this action.
  (2) Loss of AC supplied DC Power: If the AC power is lost to the base unit, the Power Indicator LED light will go off and a distinctive BUZZER sound will be emitted and continue for 5 seconds every 10 seconds. Reconnecting the power to the unit will discontinue this action.
  (3) Loss of Telephone Line Service: If there is a disconnect or a loss of telephone line service, the Telephone Line LED will go off and the same distinctive BUZZER sound as the Loss of AC Power will be emitted and continue for 5 seconds every 10 seconds. Reconnecting the telephone line service to the base unit will discontinue this action.
  (4) Internal Failure: A circuit reviews the internal operations to insure operatability. Failure to reach the prescribed voltage will present the user with an alarm.

Speakerphone: The speakerphone will continue to be active during a telephone conversation with the 9-1-1 Operator or until the operator disconnects from the line.

Phone In Use: If a user is attempting to make a base unit call and the telephone system that it's attached to is in use, the base unit will recognize the telephone system's active state and send a loud BEEPING sound through the network to indicate to others that the User is having an emergency situation. Once the line is cleared (i.e., the telephone is back on the hook), and the state of the telephone line has changed to allow a dial tone, the base unit will recognize this state of change and immediately begin its call to 9-1-1. This will continue until the base unit has been able to make the 9-1-1 call.

Busy Signal: If the base unit receives a busy signal in its attempt to call 9-1-1, the base unit will continue to redial until a connection is made. If the connection is made, but disconnected less than ten seconds into the call, the base unit will redial and call 9-1-1 until a connection is made and last more than 10 seconds.

Power Source: The system shall receive its power from a Class 2 (115 volt) power source. The base unit shall be powered using an AC Adapter with an output of DC voltage.

Tone/Pulse: The system shall have the capability to use the U.S. tone and pulse dialing systems. The switch shall be accomplished by the base unit's software system.

Prefix Use: The system shall have the capability to use a hotel or private system's dialing network with a "None, 8 or 9" prefix for activating an outside line before dialing 9-1-1. The switch shall be accomplished by the base unit's software system.

Reset: The Reset function is located on the back of the unit. Pressing it will reset the base unit's software. No customer information will be lost with this process.

Base Unit Operational Features: Some of the unique features of the 9-1-1 system's base unit include pulse/tone capability and the ability to have a prefix of none, 8 or 9 for connection to a hotel telephone system. The base also has several failsafe capabilities including low battery, power loss, telephone line loss and system malfunction indicators. It also has a 9V battery backup providing short-term power for any AC power loss. Finally, the base unit allows its customers the ability to record their personalized message and play it back for review.

With a simple, easy to push button, the customer can record their 60 second message and listen to it immediately after its been recorded. If the customer doesn't like the message, they can immediately re-record it until they get it correct. There is also a Play button that enables the user to hear the message that's been recorded anytime without losing the stored message.

The base unit also has a "reset" button, which is located on the back of the unit. Pushing a paperclip into the small hole will return the base unit to its manufacturing default settings that include its pre-recorded message.

Many other modifications of the device are possible. For example:

Integrate and communicate through and with other network systems such as Wi-Fi, Wi-Max, BlueTooth and those advancements in the near future.

The device itself may take different forms and show a variety of capabilities.

The device's internal circuit system may incorporate advancements that meet the present invention and follow-on capabilities and features.

The base unit and the wireless transmitter both could incorporate design functions that would allow it to also operate in other countries such as in Europe and Asia.

The wireless transmitter can be waterproof. If the device is used in a water environment (pool or ocean), the wireless transmitter/watch/pendant can be activated while in the water thereby transmitting a signal to the base unit which would institute its calling process.

Referring to FIG. 2, the rear of the device (100) includes a conventional modem port (16), an external telephone port (17), a system reset button (18) to allow ease of restarting should an error occur, a power switch (19), an AC/DC power coupling port (20), and a LAN connection (21) for connectivity to a broadband network. A USB coupling port (22) is located along the upper surface for receipt of the previously mentioned USB portable memory stick (07). The device includes a battery backup, batteries placed beneath battery shield (23), to allow continuous operation of the device in the event that a loss of power occurs to the AC/DC power coupling port (20).

Referring to FIGS. 3A-3E, set forth is a first embodiment of a transmitter (30) having a Call Button (31) to activate the transmitter and send a signal to the base unit starting the 9-1-1 calling sequence. A Stop Button (32) sends a transmission to the base unit to stop the 9-1-1 call. Holding the button for five seconds, along with the Stop button on the base unit digitally 'pairs' the two devices to each other. An LED Signal Indicator (33) indicates that the device is active and can be tested by pressing either the Call or Stop button. The transmitter (30) can be attached to a line (35) for hanging about the User's neck, or attached to a wrist band (36) where it can be worn like a bracelet. Alternative connection attachments allow coupling to a ring (37) for use as a key chain or a clip (38) for attachment to a belt. The transmitter includes a USB connection port (39) allowing storage of medical information. The device can be in the form of a pendant or a watch. Its operation can be activated by the keypad on the faceplate. The transmitter provides connectivity mentioned above using a DC power source embedded within its case.

Referring to FIGS. 4A-4E, set forth is a second embodiment of a transmitter (40) having a Call Button (41) to activate the transmitter and send a signal to the base unit starting the 9-1-1 calling sequence. A Stop Button (42) sends a transmission to the base unit to stop the 9-1-1 call. Holding the button for five seconds, along with the Stop button on the base unit digitally 'pairs' the two devices to each other. An LED Signal Indicator (43) indicates that the device is active and can be tested by pressing either the Call or Stop button. The transmitter (40) can be attached to a line (45) for hanging about the User's neck, or attached to a wrist band (46) where it can be worn like a bracelet. Alternative connection attachments allow coupling to a ring (47) for use as a key chain or a clip (48) for attachment to a belt. The transmitter includes a USB connection port (49) allowing storage of medical information.

Referring to FIGS. 5A-5E, set forth is a third embodiment of a transmitter (50) having a Call Button (51) to activate the transmitter and send a signal to the base unit starting the 9-1-1 calling sequence. A Stop Button (52) sends a transmission to the base unit to stop the 9-1-1 call. Holding the button for five seconds, along with the Stop button on the base unit digitally 'pairs' the two devices to each other. An LED Signal Indicator (53) indicates that the device is active and can be tested by pressing either the Call or Stop button. The transmitter (50) can be attached to a line (55) for hanging about the User's neck, attached to a ring (57) for use as a key chain or a clip (58) for attachment to a belt. The transmitter includes a USB connection port (59) allowing storage of medical information.

Referring to FIGS. 6A-6E, set forth is a fourth embodiment of a transmitter (60) having a Call Button (61) to activate the transmitter and send a signal to the base unit starting the 9-1-1 calling sequence. A Stop Button (62) sends a transmission to the base unit to stop the 9-1-1 call. Holding the button for five seconds, along with the Stop button on the base unit digitally 'pairs' the two devices to each other. The transmitter (60) can be attached to a necklace (65) for hanging about the user's neck, or attached to a ring (67) for use as a key chain. The transmitter includes a removable USB connection port (69) allowing storage of medical information.

The Critical Health Information Profile and Emergency Communication System software is resident on the web-based Critical Health Information Profile and Emergency Communication System Server which contains a Website and is installed within the base unit (100). The Critical Health Information Profile and Emergency Communication System software is designed to negotiate and communicate between the Critical Health Information Profile and Emergency Communication System server and the Critical Health Information Profile and Emergency Communication System application software. All of these are designed to communicate with each other and provide a secure link in the process. Access to this secure system requires a minimum of a telephone number, User name and a password.

Website access through a method and process specifically developed for the system, the User accesses the Critical Health Information Profile and Emergency Communication System website and creates a master account where they can:

(a) Create a Critical Health Information Profile (FIG. 7) using an easy-to-use, menu-driven sequence that allows the User to input personal and health information in a file that, once completed, is transmitted to the base unit through the server and its associated POTS/cable/Internet interface.

(b) Create an Emergency Notification List (ENL). This list is composed of a person's telephone number, email address, SMS text, or fax number that the base unit calls and notifies that the 9-1-1 system was called and activated. This is performed based on the person's requested form of communication. This may be in the form of text, fax, and verbal communication. In the verbal communication, the ENL personnel will receive a pre-canned Critical Health Information Profile and Emergency Communication System call in the form of an alert message stating that the base unit's emergency communication system has been activated.

(c) Select from a list of ancillary services and products provided by and through the Critical Health Information Profile and Emergency Communication System. These may include Critical Health Information Profile and Emergency Communication System's corporate or third party vendor products that can be purchased and uploaded to the base unit.

(d) Review important information about the Critical Health Information Profile and Emergency Communication System, corporate information and information about ancillary services and vendors.

Figure 8:
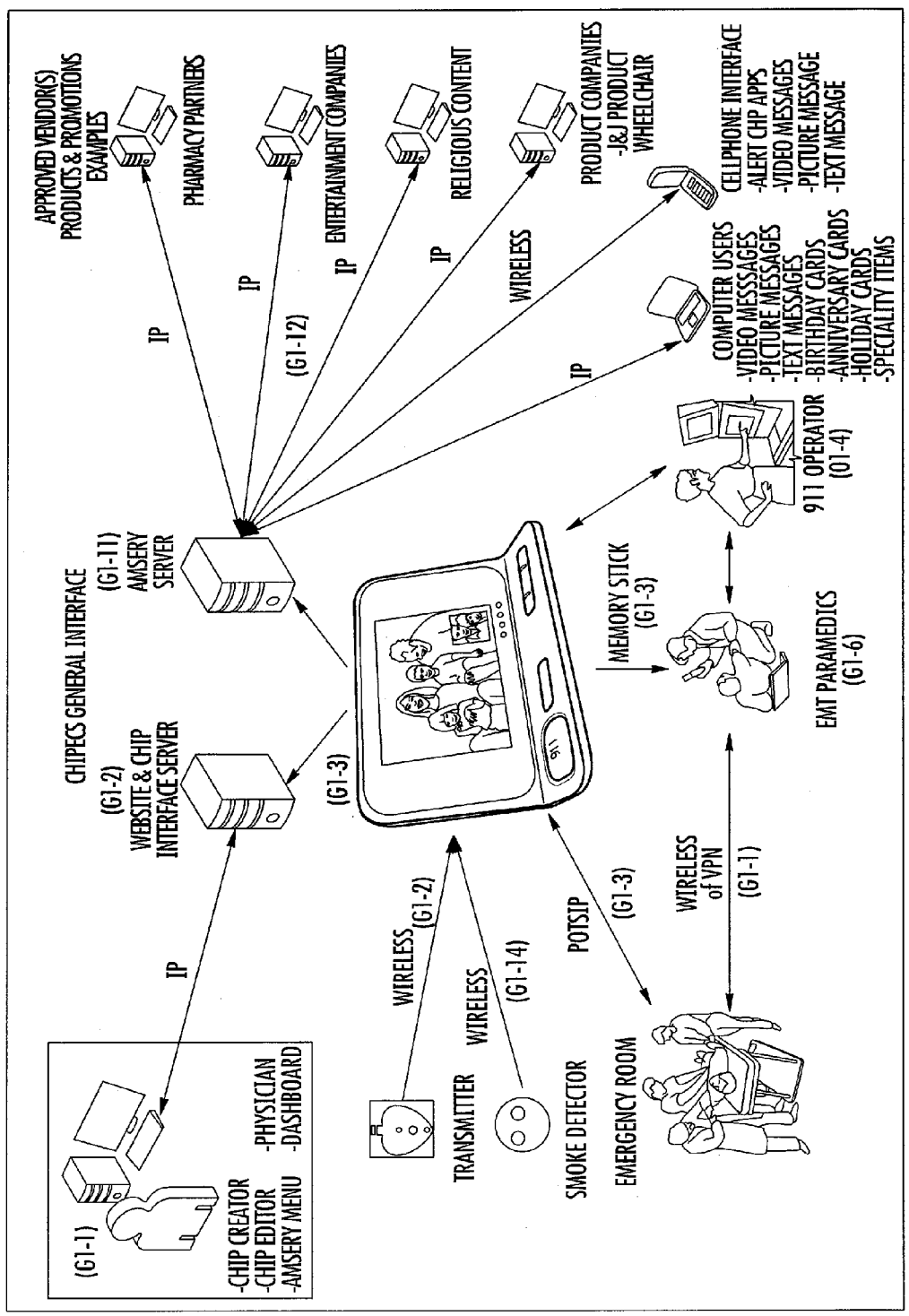
FIG. 8 illustrates the Critical Health Information Profile and Emergency Communication System General Interface and communication flow.

(e) Physician's Dashboard (FIG. 8, Single User). This area of the website is designed for the physician who desires to:

(1) Visually and verbally communicate with their Critical Health Information Profile and Emergency Communication System-based patient, (2) Review stored patient test information stored on their base unit. This shall include monthly, weekly and/or daily results from blood pressure tests, diabetes tests, asthma tests, breathing tests, and cardio tests as an example. This data will be stored and retrieved from the Patient's Dashboard and can be downloaded to the physician's legacy system.

(3) The physician can also perform remote medical testing using an advanced set of wireless medical devices that communicate from the device, through the Critical Health Information Profile and Emergency Communication System base unit, to the Physician's website. The physician can activate the medical device at the website and witness the performance of the testing from their remote location. Data derived from these tests would be presented on their website for review and analysis. Upon their need, the physician can store the acquired data on the User's Critical Health Information Profile and Emergency Communication System base unit and their own legacy system.

(4) The physician can set vital sign parameters or markers that notify them if the User's medical conditions exceed the parameters stored in the Critical Health Information Profile and Emergency Communication System base unit. Furthermore, the physician can rely on a set of algorithms designed and implemented in the Critical Health Information Profile and Emergency Communication System that provide an intuitive response in case there is a potential crisis. This 'intuitive' response will monitor the User's stored vital sign data stream over a prescribed period of time, graph the results, and notify the physician ahead of time if the accumulative result trend toward a growing, potential crisis. This function allows the system to perform a basic evaluation of the User's physical condition without the need of a nurse.

Figure 9:
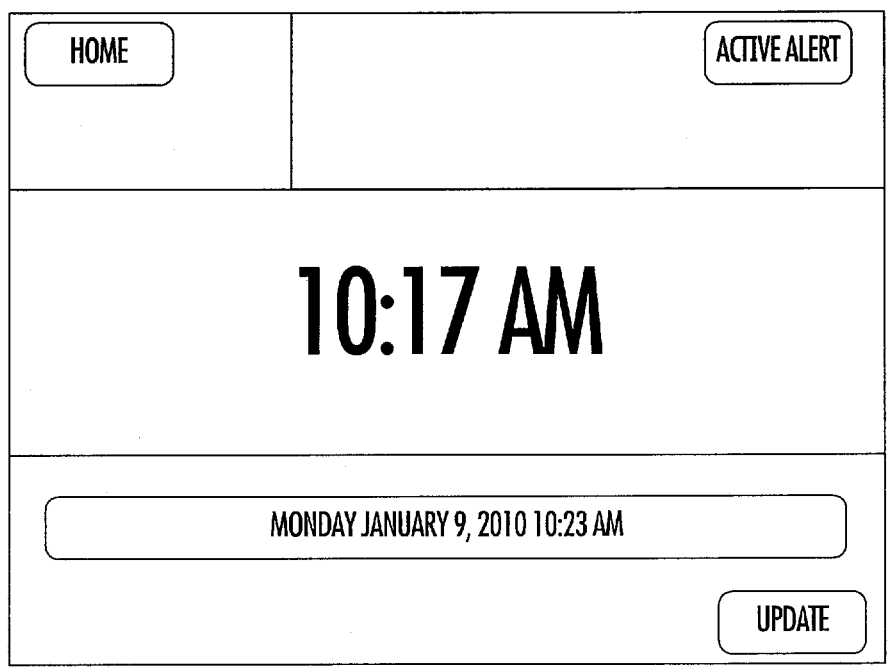
FIG. 9 illustrates the base unit's 'Splash' page.

The Critical Health Information Profile and Emergency Communication System Base Unit Application Software, using its customized browser-based system, operating over a selected operating system designed for the device, the base unit presents the User with a multitude of easy-to-use functions and capabilities. These include:

(a) A splash screen (FIG. 9) composed of:

(i) an analog or digital clock, with an alarm that can be activated by the user using drop down menus.

(ii) Weather information based on the User's zip code that has been extracted from the User's Critical Health Information Profile Critical file.

(iii) Up to five GUI's representing phone numbers important to the User. In this case, the User may have included the names of their doctor, relative or other important persons that can be called by simply pressing the GUI representing the person. The process calls the person requested by the User.

(iv) Pressing the Splash Page screen sends the user to the next level in the software architecture.

Figure 10:
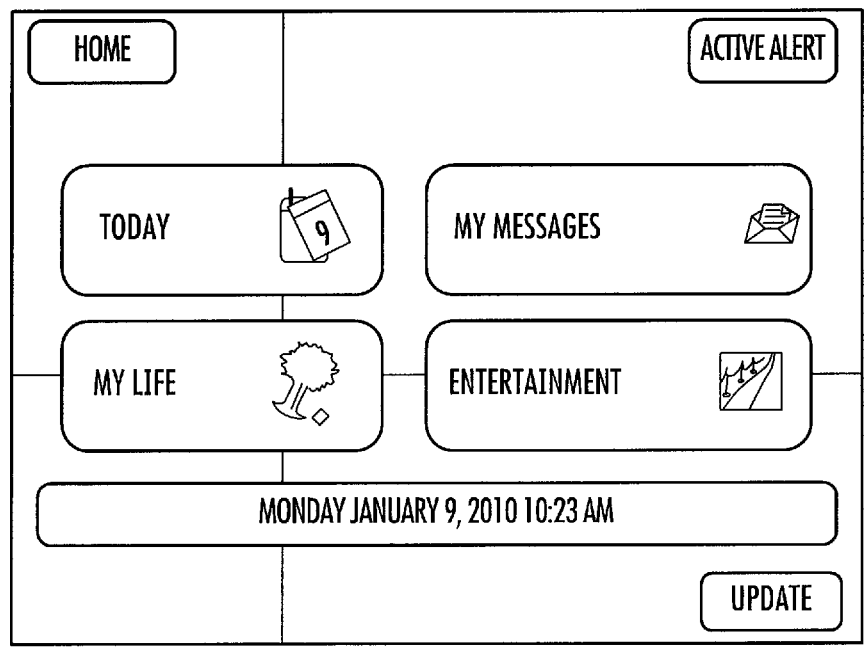
FIG. 10 illustrates the base unit's 'Main' page.

(b) Main Interface for the User: (FIG. 10) includes access to folders pertaining to specific information and data. Each level has been design for simplicity and use, as a majority of its customers and Users will be seniors. The page also includes a 'Home' GUI which sends the senior back to the Splash Page. The Main Page includes program folders called 'Today', 'My Life', 'Entertainment' and 'Message'. Pressing any one of the GUI representing the above folders sends the User to that specific file.

Figure 11:
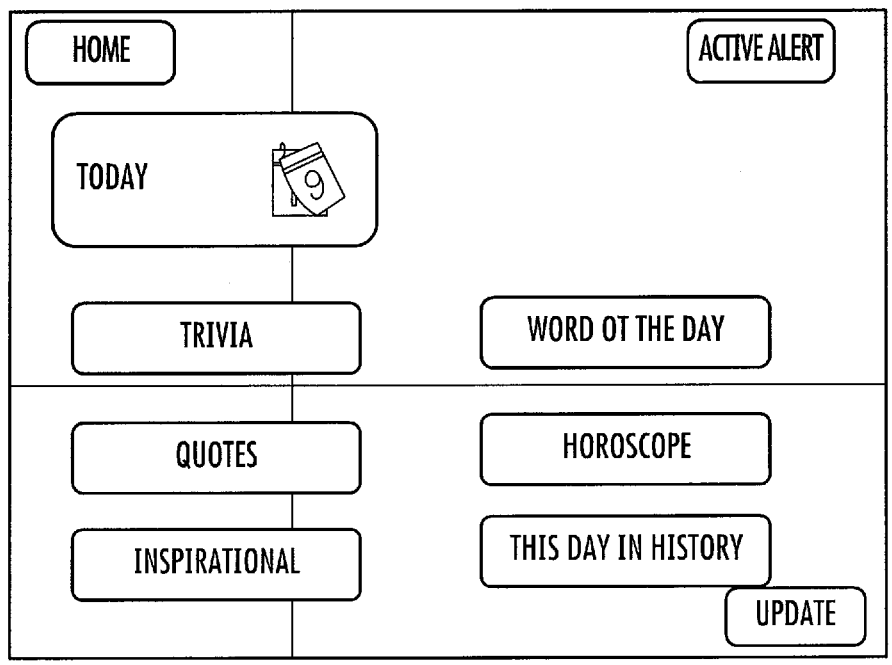
FIG. 11 illustrates the base unit's 'Today' page.

(c) Today Folder: (FIG. 11) provides several programs for the User. These include Trivia, Horoscope, Inspirations, Word of the Day, Quote of the Day and other free User desired programs. A 'Home' icon, when pressed, sends the User back to the Main Page. If the user doesn't perform any functions after three minutes, the computer automatically sends the User back to the Splash Page screen.

Figure 12:
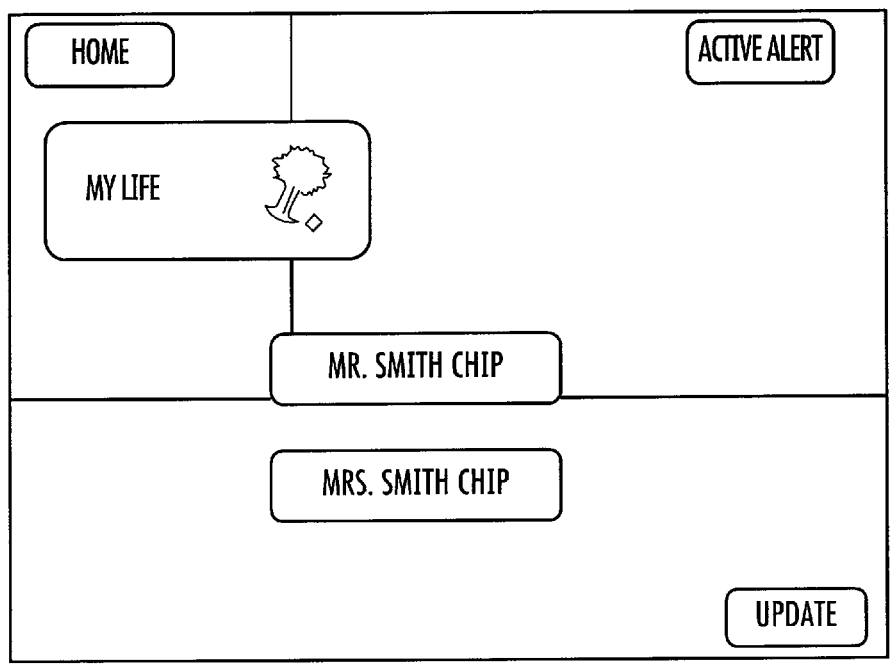
FIG. 12 illustrates the base unit's 'My Life' page.

(d) My Life: (FIG. 12) This folder contains important information regarding the personal health of the User(s). Here is where the Critical Health Information Profile(s) is located. The Patient 'DASHBOARD' is also located here.

Figure 7:
FIG. 7 illustrates a personal health record file as seen on a computer.

(1) Critical Health Information Profile (FIG. 7). A GUI icon representing the User(s) Critical Health Information Profile shows a picture of the User, their name and age. A maximum of 4 Critical Health Information Profile icons can be presented here. When pressed by the User, the program sends the User to the Critical Health Information Profile file containing their personal and medical information file which is presented on the LCD screen for review.

(2) The Critical Health Information Profile software located on the base unit is Health Level-7 (HL7) compliant enabling it to seamlessly communicate with major hospital legacy networks worldwide. This singular process allows for an expedient, efficient processing of critical personal health information in a time of crisis. Under current, normal process, the emergency responders would verbally communicate with the arrival hospital the possible medication and condition of the incoming patient. With the Critical Health Information Profile and Emergency Communication System Critical Health Information Profile, the User's Critical Health Information Profile information would be fed directly into the hospital legacy system, processed and presented to the arriving physician in a form and structure as defined by the legacy system. This new process provides for greater accuracy and expediency not seen by any system on the market today.

(3) The information stored in the base unit's Critical Health Information Profile is provided by an efficient method and process developed between the Critical Health Information Profile and Emergency Communication System website, its servers, and the User's base unit. The method allows the User to create an account on the website where they are led through a series of questions designed to produce valuable medical and personal information for use by emergency responders. Once the Critical Health Information Profile are completed on the User's website, the process allows the User to send it by means of a communication link between the two devices. Pressing the 'SEND' function on the LCD touch screen, the software connects and transmits data to the User's Critical Health Information Profile and Emergency Communication System base unit through one of a multitude of communication networks including POTS, cable, and the Internet.

(4) Retrieval of Critical Health Information Profile information. This functional capability provides a method and system that can retrieve and transmit User-stored personal and health information by emergency responders at the point of care. The process of presenting the information occurs simultaneous upon connection with the 9-1-1 Operator. Presented on the base unit's LCD screen are the Critical Health Information Profile GUI icons representing those User files stored in the unit. Using the base unit's LCD touch screen, the emergency responder can access the User's Critical Health Information Profile file, review the data for pertinent information and then transmit that data to a designated receiving hospital or medical center. Its process is accomplished through the base unit's microprocessor-based system and memory storage subsystem so that a customer (User) can securely store, access and remotely retrieve their personal and health information at any time of the day and transmit it to a receiving hospital or medical center by either themselves or a designated person such as an emergency responder. The method of transmission includes the ability to send the Critical Health Information Profile via fax, email, SMS text, web-based and other methods in a multitude of formats including but not limited to HL7 compliant text, plain text, Adobe acrobat format, and other future formats as required by medical facilities.

The Critical Health Information Profile and Emergency Communication System base unit also contains a USB-enabled memory stick that contains an exact duplicate of the User's Critical Health Information Profile. In the event that transmission of a User's Critical Health Information Profile to a medical center is not possible, the memory stick can be extracted from the base unit for transportation by the emergency responder. The memory stick contains a User's Critical Health Information Profile in a multitude of formats including but not limited to HL7 compliant text, plain text, Adobe pdf, and other future formats as required by medical facilities. The memory stick can be re-inserted into the base unit. Once inserted, the base unit software will recognize the memory stick and sync with its on-board software to upload the latest Critical Health Information Profile.

Figure 13:
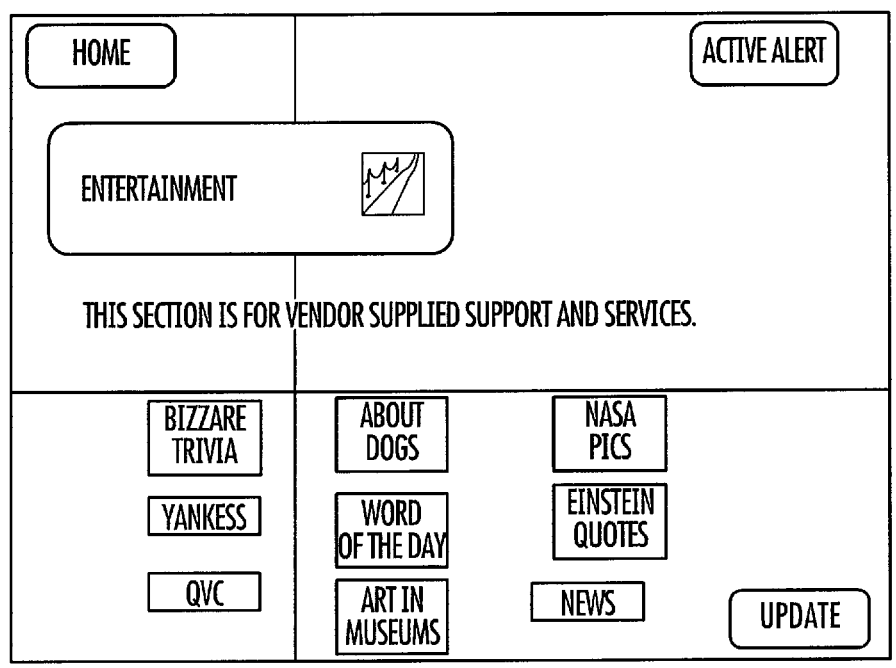
FIG. 13 illustrates the base unit's 'Entertainment' page.

Entertainment Icon. (FIG. 13) This folder contains Critical Health Information Profile and Emergency Communication System corporate and third party vendor supplied entertainment and other programs designed for User's pleasure. These programs are selected and downloaded by the User. Their activation and use is determined by the vendor-supplied interface. Upon completion of the program, the User is returned to their Entertainment page for further action. The 'Home' icon sends the user to their Main page.

Figure 14:
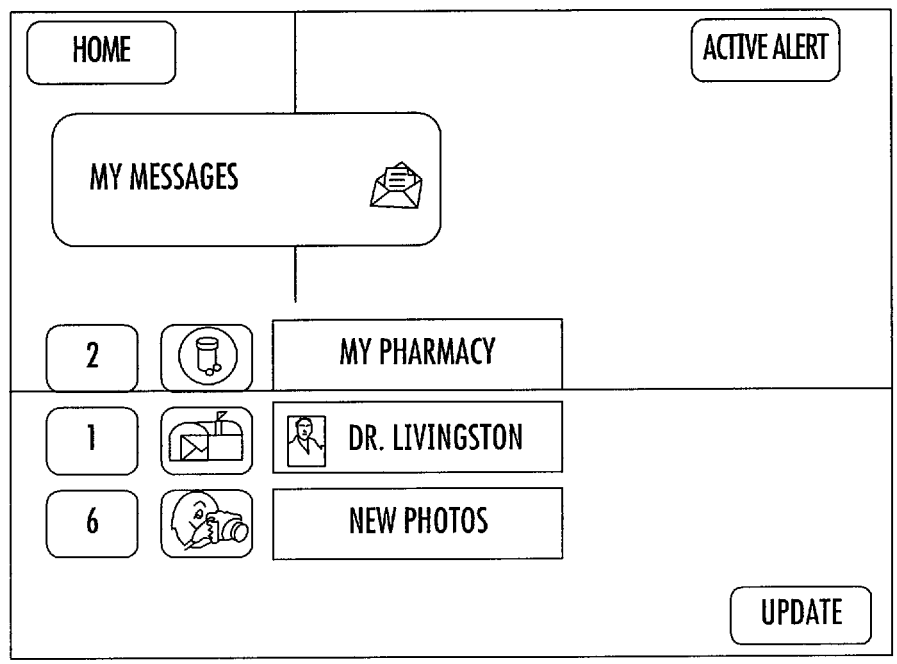
FIG. 14 illustrates the base unit's 'Message' page.

Messaging Icon. (FIG. 14) This folder contains a messaging program that allows the User to receive and transmit messages in the form of text, video, audio and pictures. It is similar in design to those on the market today, but is developed with the senior in mind. The User can review, store, and delete these on the base unit. Once the User has completed their review of their messages they are returned to the Main screen.

Critical Health Information Profile and Emergency Communication System incorporates other advanced software features including:

The Patient's Dashboard—a Critical Health Information Profile and Emergency Communication System base unit application that permits patients to perform their own medical updates, such as daily blood pressure test and record their results in the Critical Health Information Profile and Emergency Communication System based system for future use and evaluation by themselves and patient-authorized personnel, and automated messaging service that (a) provides a multitude of patient-centric services such as helpful reminders, prescription refills and ready-for-pickup notification, daily timed medication intake, physical testing and recording of blood pressure, diabetes, asthma, cardio, and other physician required analysis.

Applications designed to perform specific medical tests, such as those listed above, that (a) interface with Critical Health Information Profile and Emergency Communication System-designed wireless medical devices, and (b) perform functions such as record, store, review and graphically present the results on the Critical Health Information Profile and Emergency Communication Systems touch screen, thus (c) allowing approved personnel, such as a physician, the ability to access and download their patient's data to their computer system.

Figure 15:
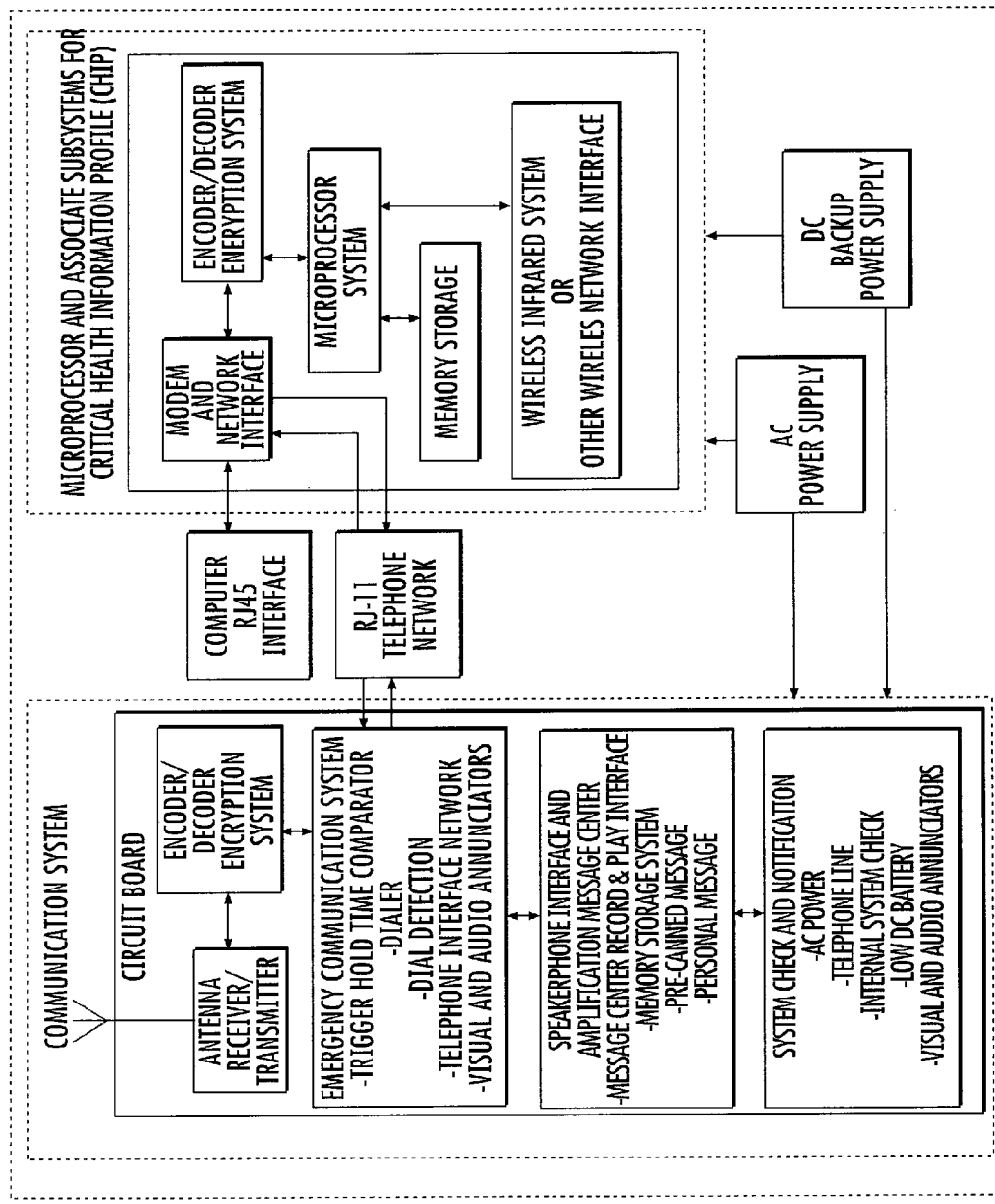
FIG. 15 illustrates an electronic block diagram of the base unit of the instant invention.
Figure 16:
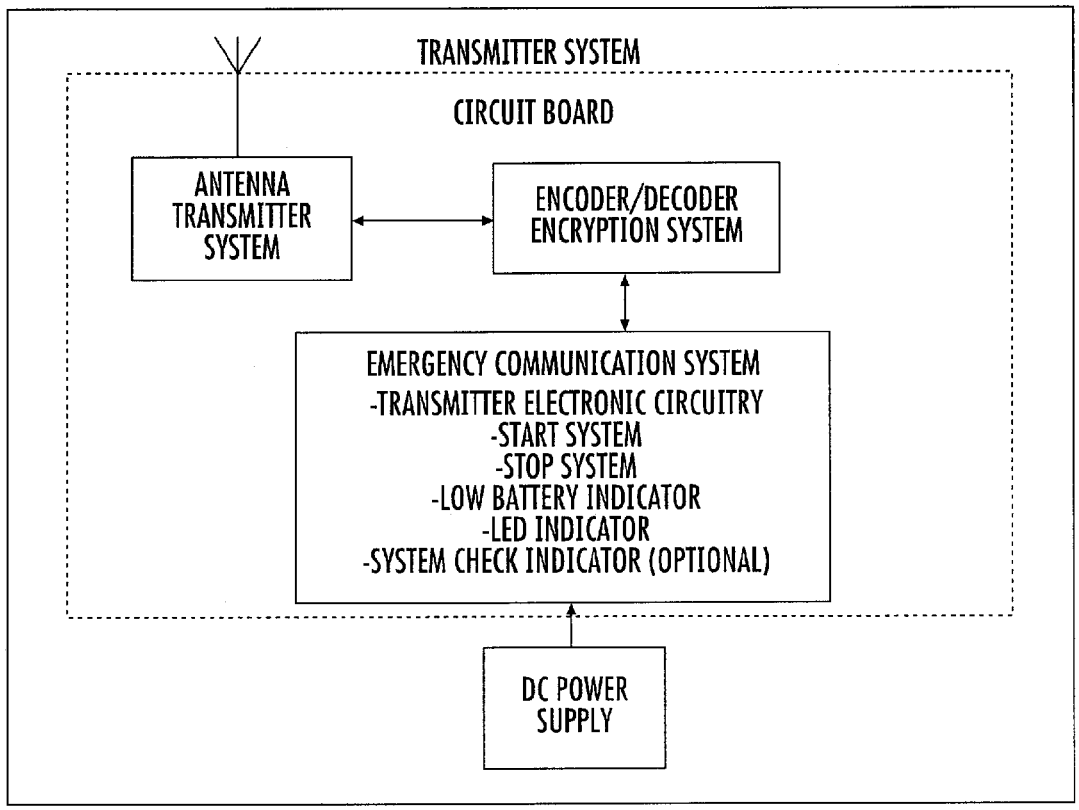
FIG. 16 illustrates an electronic block diagram of the wireless transmitter of the instant invention.

OPERATIONS—The following describes the operational use of the Critical Health Information Profile and Emergency Communication Systems Critical Health Information Profile subsystem and the emergency communication system. While the operations are described below, it is assumed that the process of its' use could be changed or modified to meet the continual evolution of technology. Referring to FIGS. 8, 15-16:

(GI-1) Home, office or mobile computer system. This permits authorized users to communicate with the base unit (GI-3). This is accomplished by the user logging on to the Critical Health Information Profile and Emergency Communication System's website. Once the server (GI-2) validates the user's account, it will permit access to the Critical Health Information Profile and Emergency Communication System.

(GI-2) Critical Health Information Profile and Emergency Communication System website and Critical Health Information Profile interface. This web-based server serves as the interface control to the Critical Health Information Profile and Emergency Communication System. It provides validation of accounts and permits communications between account managers (GI-1) and their associated base unit (GI-3).

(GI-3) The Critical Health Information Profile and Emergency Communication System base unit. This device stores user supplied information such as their personal Critical Health Information Profile data. It can be accessed by authorized users to create and update critical Health Information Profile data and other information important to the user. It also presents Critical Health Information Profile information once the 9-1-1 operator answers the call. The information is displayed on the LCD touch screen and can be accessed by paramedics or other authorized persons. This information can be sent to a hospital through the Critical Health Information Profile and Emergency Communication System's dialing software.

(GI-4) 9-1-1-Operations. The 9-1-1 operator is contacted by the base unit (GI-3) by the activation of the base unit's 9-1-1 button or through the activation of the transmitter (GI-9) which further activates the 9-1-1 call on the base unit. The operator can communicate with the user through the base unit's microphone/speaker system by pressing '0' on their telephone system.

(GI-5) Portable Memory Stick. This is a device that stores an exact duplicate of the user's Critical Health Information Profile information in multiple formats. The memory stick can be extracted from the base and transported.

(GI-6) Paramedics have access to the user's Critical Health Information Profile information either by using the base unit's (GI-3) touch screen or by extracting the memory stick and acquiring the information as needed.).

(GI-7) The base unit has the capability to transmit information to the awaiting hospital by several means. These include email, fax, modem, and text. There is no limit to the methods by which this information can be transmitted.

(GI-8) The Emergency Responder can transmit the user's Critical Health Information Profile information either through the methods as described above in GI-6 or through their own handheld communication system that has the ability to download Critical Health Information Profile information.

(GI-9) Wireless Transmitter. This device, when activated, sends a signal to the base unit (GI-3) which starts the sequence to call 9-1-1.

(GI-10) Smoke Detector. This system can recognize a signal from a smoke detector to the base unit (GI-3) and start the sequence to Call 9-1-1.

(GI-11) AMSERV Server. This subsystem permits the user to receive ancillary information from a multitude of vendors and suppliers. It is processed by the account manager through the Critical Health Information Profile and Emergency Communication System's website.

(GI-12) AMSER vendors. A multitude of approved vendors can interface with the base unit (GI-3) through the AMSER server (GI-11). These products would be displayed on the base unit (GI-3) for the user's review.

Software for the Critical Health Information Profile Subsystem. Customer accessing the Critical Health Information Profile subsystem on the base unit.

The customer (GI-1) will create their own Critical Health Information Profile by connecting through and interfacing with the Website (GI-2). This is accomplished by a customer using their own home/office/laptop computer system and communicating either through the World Wide Web or by POTS to interface with the Website. This software will use the latest in web technology to enable a seamless interface with its customer and the base unit (GI-3). The customer simply accesses their base unit through the Website, inputs their telephone number, user name and password. Once the information is provided, the Website's software will contact user's base unit's telephone interface subsystem using the telephone number provided. If the secure information is correct, the Website will connect to the user's CHIP's subsystem on the base unit. There, the Website software will allow the customer (GI-1) to create a critical health information profile, upload and store that information to the Critical Health Information Profile subsystem on their base unit (GI-3). Once created, the customer can access, edit, delete or update their Critical Health Information Profile at any time. The system will allow a maximum of 15 records to be stored on one base unit (GI-3).

Emergency Responders accessing the Critical Health Information Profile subsystem in the base unit. In an emergency situation, the emergency responder will access the customer's Critical Health Information Profile through the LCD touch screen on the base unit (GI-3). There, they will access the Critical Health Information Profile through the graphic interface icon. Touching the icon will permit the emergency responder to access the customer's stored Critical Health Information Profile and use it for life saving events. The Critical Health Information Profile software will also allow the emergency responder to 'forward' the information to the receiving hospital or medical center. This can easily be accomplished by touching the icon representing the 'send to' application. Once the icon is activated, the Critical Health Information Profile software will present a telephone dial pad with all known standard digits. The emergency responder will dial the number of the receiving center's computer-based database system. Once connected, the CHIP's subsystem will upload the customer's Critical Health Information Profile to the receiving center. The Critical Health Information Profiles is HL-7 software compliant and allows for direct connection, interface, and seamless creation of a patient record with any hospital or medical center who is also HL-7 compliant.

The operation of the Emergency Communication System: The device's system is composed of a base unit (GI-3), which is connected to the standard U.S. telephone system, and a wireless transmitter (GI-9) in the form of a watch or pendant that is worn by its user in the form of a hanging pendant or a watch. The wireless transmitter's main purpose is to send an emergency signal to the base unit (GI-3) commanding it to activate its system, which in turn, dials 9-1-1 and allows for the playing of its pre-recorded or personalized message once the operator has answered.

Upon activation of either the base unit (GI-3) or the remote wireless unit (GI-9), the system will perform the necessary functions to dial 9-1-1 and transmit the appropriate user messages. The base unit (GI-3) has an audible alarm that continues to operate (per user's manual) until the operator presses "0" to access the base unit's speakerphone system. The speakerphone system enables the 9-1-1 operator to have two-way communication with the user if they are available.

Additional Software Functions within the Base Unit include:

1. An audible alarm and a set of lights indicate either/or:
   A. Power: The loss of AC Power.
   B. Tel Line: The loss of the telephone line.
   C. System: The failure of the Model 9-1-1A base unit.
   D. Battery Low: The 9V battery is low and should be replaced.
2. CALL 9-1-1 and STOP button
   A. Call 9-1-1 Button
      a. Activates the system to dial 9-1-1 and begin recording
      b. Button has back lighting for use at night
      c. Button flashes bright when in operation
   B. Stop Button (Long Oval-ended Button)
      a. Stops outgoing call to 9-1-1.
      b. Button has letters that are backlit.
      c. Used to 'pair' additional transmitters (GI-9) with the base unit (GI-03).
3. Connection to the telephone or broadband-based telephone systems (FIG. D). A dedicated line is recommended.
4. If the system is in use, the base unit (GI-3) will have the ability to send an audible alarm sound through the telephone system to indicate to others that the base unit is attempting to make an emergency call.
5. If the "in-line" telephone is in use, the base unit (GI-3) will disrupt and disconnect the line and allow the base unit to make its emergency call to 9-1-1.
6. Ability to dial 9-1-1 using DTMF or pulse dialing using software switch within the base unit (GI-3).
7. Ability to select either "no prefix" or an "8" or a "9" through a software switch in the base unit (GI-3). This will permit the user to use the base unit in a PBX environment.
8. When the system is activated, audio and visual alarms will sound.
9. Message Record System
   A. Provides the customer the ability to record and re-record a short (60 second) message.
      a. Customer presses and holds RECORD button to record message. Once message is recorded and button is released, the customer will hear a playback of their message. The message may be recorded over by simply pressing the button and holding it again.
      b. The customer may press the PLAY button any time to hear the recorded message. Both the pre-recorded and personal message may be played back through the pressing of this button.
      c. Provides the customer with a standard "emergency" message which records a 60 second message.
10. Ability to have the 9-1-1 operator discontinue the repetitive message by keying in a "0" code. Once this is accomplished, the 9-1-1 operator can converse with the person requesting emergency assistance through a built-in speakerphone and speaker system (speaker-phone and volume button) on the base unit.
11. Once Operator discontinues the call, the emergency alarm will also discontinue.
12. For security purposes, the system can be put in silent mode (switch-able) that stops the system's audio alarm, lights flashing and speakerphone. While the speakerphone may not operate, this does not prevent the Operator from listening in on conversations in the background. This is very important for storeowners who may have a serious criminal problem in progress.

Detailed embodiments of the instant invention are disclosed herein, however, it is to be understood that the disclosed embodiments are merely exemplary of the invention, which may be embodied in various forms. Therefore, specific functional and structural details disclosed herein are not to be interpreted as limiting, but merely as a basis for the claims and as a representation basis for teaching one skilled in the art to variously employ the present invention in virtually any appropriately detailed structure.

All patents and publications mentioned in this specification are indicative of the levels of those skilled in the art to which the invention pertains. All patents and publications are herein incorporated by reference to the same extent as if each individual publication was specifically and individually indicated to be incorporated by reference. It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What I claim is:

1. A critical health information profile and emergency communication system, comprising:
   a base unit including
      a microphone;
      a speaker;
      a user interface;
      a communication system comprising an interface for communicating via a telephone system and or a broadband network;
      a memory system;
      an extractable portable memory embedded in said base unit, said portable memory separate from said memory system, said extractable portable memory being configured to be accessible from the exterior of said base unit and extractable from said base unit by emergency responders;
      a microprocessor coupled to said communication system, said memory system, and said extractable portable memory when said extractable portable memory is embedded in said base unit, said microprocessor configured with software that operates to receive an input to said base unit indicating to retrieve a previously stored critical health information profile of a user from a remote location and based on said input receive at said base unit the previously stored critical health information profile of the user via said communication system, store the critical health information profile in said memory system, and automatically store a duplicate of the critical health information profile in said extractable portable memory in multiple formats, the critical health information profile comprising medical history information of a user, wherein the critical health information profile is HL-7 compliant and the duplicate of the critical health information profile is stored in the extractable portable memory in multiple formats including HL-7 and plain text, said microprocessor further configured to store an emergency notification list that includes contact information of people that the base unit calls and notifies that the 9-1-1 system was activated;

a display screen;

a case holding said communication system, memory system, extractable portable memory, microprocessor, display screen, and user interface, said case comprising a coupling port on a surface of case for receiving said extractable portable memory; and at least one preprogrammed hot button, said base unit configured to, upon actuation of said hot button:
call a 9-1-1 operator and play the pre-recorded message stored in said memory system to the 9-1-1 operator,
communicate the critical health information profile including the medical history stored in said memory system to the 9-1-1 operator in a format displayable on the 9-1-1 operator screen,
allow two-way voice communication between the 9-1-1 operator and a user at said base unit using said microphone and said speaker,
automatically call the people on the emergency notification list and play an alert message stating that the base unit's emergency communication system has been activated; and
receive inputs via said interface to display the critical health information profile including said received medical history on said display screen of said base unit.

2. The critical health information profile and emergency communication system according to claim 1, wherein said base unit is configured to receive a signal from a wireless transmitter to operate said hot button.

3. The critical health information profile and emergency communication system according to claim 2, wherein said wireless transmitter is configured to be worn on an arm.

4. The critical health information profile and emergency communication system according to claim 2, wherein said wireless transmitter is configured to be worn around a neck.

5. The critical health information profile and emergency communication system according to claim 1, further comprising a means to create, edit, delete, store, upload and retrieve the critical health information profile.

6. The critical health information profile and emergency communication system according to claim 5, further comprising a website configured to create and edit the critical health information profile, and wherein said base unit is configured to receive the critical health information profile from the website.

7. The critical health information profile and emergency communication system according to claim 1, wherein said base unit further comprises a means for transmitting the critical health information profile to a medical center or hospital through email, fax, or text.

8. The critical health information profile and emergency communication system according to claim 1, wherein said base unit further comprises an AC/DC power supply, a circuit-testing module, and a visual alarm annunciator, said circuit-testing module configured to energize said visual alarm annunciator upon failure of either said AC or DC power supply.

9. The critical health information profile and emergency communication system according to claim 1, further comprising a means to enable medical personnel to review, update, download and analyze vital sign data of a user stored in the base unit, and a means for setting notification parameters to said vital sign data.

10. The critical health information profile and emergency communication system according to claim 9, wherein the vital sign data includes blood pressure, cardio, and diabetes information.

11. The critical health information profile and emergency communication system according to claim 1, further comprising an input/output means for connecting said base unit to a conventional telephone line or a broadband-based telephone system.

12. The critical health information profile and emergency communication system according to claim 1, wherein said at least one preprogrammed hot button is a large dome-base illuminated emergency call key.

13. The critical health information profile and emergency communication system according to claim 1, wherein said base unit further comprises a video camera, and said base unit is further configured to enable a 9-1-1 operator to view the user after actuation of the preprogrammed hot button.

14. A method of providing emergency communications, the method comprising:
receiving at a base unit a populated critical health information profile of a user from a remote storage location, the critical health information profile comprising medical history information;
storing a critical health information profile of a user in a memory system of the base unit and automatically storing a duplicate of the critical health information profile in multiple formats on a portable memory that is extractably coupled to the base unit via a port on a surface of the base unit, wherein the critical health information profile is HL-7 compliant and the duplicate of the critical health information profile is stored in the extractable portable memory in multiple formats including HL-7 and plain text;
storing an emergency notification list on the memory system of the base unit, the emergency notification list including contact information of people that the base unit calls and notifies that the 9-1-1 system was activated;
calling a 9-1-1 operator upon actuation of a preprogrammed hot button, and automatically
playing a pre-recorded message, stored in said memory system, to a 9-1-1 operator;
communicating the critical health information profile including the medical history stored in said memory system to the 9-1-1 operator in a format displayable on the 9-1-1 operator's screen,
connecting two-way voice communication between the 9-1-1 operator and the base unit;
calling the people on the emergency notification list and playing an alert message stating that the base unit's emergency communication system has been activated; and
displaying controls on a touch-screen of the base unit to display the received critical health information profile on a display screen of the base unit.

15. The method of claim 14, wherein the base unit comprises a speaker phone for two-way voice communication between the 9-1-1 operator and the base unit.

16. The method of claim 14, further comprising selecting the pre-recorded message from a pre-canned message or a recording of a personalized message.

17. The method of claim 16, wherein playing a pre-recorded message comprises playing the pre-recorded message repeatedly to the 9-1-1-operator, and wherein the method further comprises stopping the playing of the pre-recorded message upon receiving a signal from the 9-1-1 operator allowing the operator to verbally communicate with the user.

18. The method of claim 14, further comprising activating the preprogrammed hot button by a wireless transmitter.

19. The method of claim 14, wherein the method further comprises delaying calling the 9-1-1 operator for a pre-selected time interval after the preprogrammed hot button is activated, and displaying a visual annunciator on the base unit and sounding an audio annunciator from the base unit to indicate that a 9-1-1-call has been requested.

20. The method of claim 14, further comprising enabling a silent mode of the base unit which dials 9-1-1 immediately and allows the operator to 'listen in' on the conversation through a speakerphone.

21. The method of claim 14, further comprising including a step of interfacing with a modem to connect to an emergency communication system.

22. The method of claim 14, further comprising logging of those emergency responders who have accessed the base unit's critical health information profile information on the base unit.

23. The method of claim 14, providing an editing interface on the base unit to change information or add additional information to records of a user stored on the base unit memory and on the portable memory.

24. The method of claim 14, wherein receiving the critical information profile of a user comprises receiving the critical information profile of a user from further comprising an Internet based storage system.

25. The method of claim 14, further comprising encrypting the critical health information profile.

26. The method of claim 14, further comprising storing User name and password in reference to the User's telephone number.

27. The method of claim 14, further comprising accessing the critical health information profile-from the USB memory stick.

* * * * *